(12) United States Patent
Yamagishi et al.

(10) Patent No.: US 8,557,224 B2
(45) Date of Patent: *Oct. 15, 2013

(54) ORAL CAVITY COMPOSITION

(75) Inventors: Atsushi Yamagishi, Tokyo (JP); Atsushi Takayanagi, Tokyo (JP)

(73) Assignee: Kao Corporation, Tokyo (JP)

( * ) Notice: Subject to any disclaimer, the term of this patent is extended or adjusted under 35 U.S.C. 154(b) by 223 days.

This patent is subject to a terminal disclaimer.

(21) Appl. No.: 10/564,368

(22) PCT Filed: Jul. 14, 2004

(86) PCT No.: PCT/JP2004/010014
§ 371 (c)(1),
(2), (4) Date: Jan. 12, 2006

(87) PCT Pub. No.: WO2005/004824
PCT Pub. Date: Jan. 20, 2005

(65) Prior Publication Data
US 2006/0171903 A1   Aug. 3, 2006

(30) Foreign Application Priority Data
Jul. 15, 2003   (JP) .................................. 2003-197096

(51) Int. Cl.
*A61K 8/21* (2006.01)
*A61K 8/00* (2006.01)
*A61K 8/46* (2006.01)

(52) U.S. Cl.
USPC ............... 424/52; 433/216; 433/215; 424/49; 424/57

(58) Field of Classification Search
USPC ........... 424/53, 52, 49, 57; 433/215, 216, 223
See application file for complete search history.

(56) References Cited

U.S. PATENT DOCUMENTS

| 4,048,300 A | * | 9/1977 | Tomlinson et al. ............. 424/52 |
| 4,083,955 A | | 4/1978 | Grabenstetter et al. |
| 4,397,837 A | | 8/1983 | Raaf et al. |
| 5,605,675 A | | 2/1997 | Usen et al. |
| 5,882,630 A | * | 3/1999 | Gates et al. .................... 424/49 |
| 6,287,120 B1 | * | 9/2001 | Wiesel .......................... 433/215 |

FOREIGN PATENT DOCUMENTS

| JP | 49-94187 | | 9/1974 |
| JP | 58-219107 | | 12/1983 |
| JP | 04-217904 | | 8/1992 |
| JP | 05-255029 | | 10/1993 |
| JP | 2000-504037 | | 4/2000 |
| JP | 2001-500144 | | 1/2001 |
| JP | 2001-523217 | | 11/2001 |
| JP | 2002-505261 | | 2/2002 |
| WO | WO9813012 | * | 4/1998 |
| WO | WO 99/34772 | | 7/1999 |

OTHER PUBLICATIONS

Forward, G.C., Non-fluoride anticaries agents, Adv. Dent. Res., 1994, 8(2), pp. 208-214.*
"Tooth Wear and Dentin Hyperesthesia", translated by Kenichi Kobayashi, et al., Ishiyaku Publishers, Inc., Jan. 20, 2003, pp. 357-361(English Translation by machine).

* cited by examiner

*Primary Examiner* — Lezah Roberts
*Assistant Examiner* — Tracy Liu
(74) *Attorney, Agent, or Firm* — Oblon, Spivak, McClelland, Maier & Neustadt, L.L.P.

(57) ABSTRACT

The present invention provides an oral cavity composition with which brief treatment using the same yields a high effect for dental cavity prevention and an excellent dental hyperesthesia preventive and treatment effects, and a method of treatment using such a composition. The oral cavity composition according to the present invention contains a first composition (A) containing a fluoride ion-supplying compound, an inorganic phosphoric acid and a salt thereof, and a second composition (B) containing a calcium salt of organic acid, with an organic acid constituting said calcium salt of organic acid having a pKa value ranging from 3 to 11, or at least one pKa value ranging from 3 to 11 when said organic acid has plural pKa values, wherein said first composition (A) and said second composition (B) are discretely packed from each other so that said two compositions can be alternately used and then come to be mixed with each other at a tooth region when applied thereto.

17 Claims, No Drawings

ORAL CAVITY COMPOSITION

FIELD OF THE INVENTION

The present invention relates to an oral cavity composition allowing for a shorter treatment period, prevention of tooth decay, and efficient prevention or treatment of dentin hyperesthesia.

BACKGROUND OF THE INVENTION

As methods effective for the prevention of tooth decay, there are several means known to date, such as (1) strengthening the acid resistance of teeth to render their constituents harder to elute in acid, which represents one of the direct causes of dental caries, and (2) facilitating the remineralization process on teeth to compensate for their eluted constituents at a higher rate.

Since fluoride acts to turn hydroxyapatite which is a major constituent of teeth into a fluoroapatite to render the constituent hard to elute in acids and is highly effective for facilitating the formation of hydroxyapatite to thereby facilitate the remineralization of teeth, it has become common at dental clinicals to coat teeth with a fluoride as treatment for preventing dental caries. In such cases, the most commonly used fluoride formulation is an acidulated phosphate fluoride solution (hereinafter referred to as APF).

However, the APF treatment takes a long time to complete the formation of calcium fluoride, because it includes a process which facilitates the double decomposition of teeth by the action of an acid and then exploits calcium contained there to produce calcium fluoride for fluoride uptake into the teeth. Specifically, for this method of treatment, it has been necessary that APF is first applied onto human teeth to be left as it is for 4 minutes, and further, the eating and/or drinking is forbidden for additional 30 minutes or longer. In this case, a person undergoing the care or treatment is required to exercise patience in keeping his or her mouth open for 4 minutes after APF application, and further, such a patient subjected to the treatment may feel rather burdensome because APF has a nasty taste due to its strongly acidic taste. Especially, for patients who are children, such a bad taste might be more burdensome.

On the other hand, as periodontal disease patients increase in number, dentin hyperesthesia caused by a stimulus occurring when eating and/or drinking something hot or cold and transferred directly to pulp nerves due to exposed dentin at dental roots has now become a problem to be seriously dealt with. To prevent or treat this dentin hyperesthesia, it is necessary to block the transmission of external stimulus by heat, acids, or etc. to pulp nerves by obturating dental canaliculi present in dentin.

While it has so far been done as preventive and curative treatment for dentin hyperesthesia to apply a 5% sodium fluoride varnish coating onto teeth, such application treatment is not free from problems yet, in that this method uses calcium contained in teeth and saliva to obturate the dental canaliculi and it takes time for calcium to turn to its fluoride and thus a longer time elapses before the dental canaliculi is effectively obturated, or in that the effect of the treatment has a low persistence after application (cf. the nonpatent literature 1.)

The patent literature 1 given below discloses a product for the remineralization of dental enamel, containing a first separate ingredient containing a water-soluble calcium salt, and a second separate ingredient containing a phosphate and at least one water-soluble fluoride salt that produces fluorine ions. However, the mineralization product disclosed in the patent literature 1 is taught to be "applied as a mixture prepared by mixing the first and second solutions together" (cf. the patent literature 1, page 19, lines 3 to 4).

In this regard, in a case where the first and the second liquids are first mixed together and then the resultant mixture is applied on to the teeth, there has been a problem that it is difficult to form calcium phosphates selectively on a tooth surface, because if the first solution containing a water-soluble calcium salt is mixed with the second solution comprising a phosphate and a water-soluble fluoride salt, such calcium phosphates (including partially fluorinated salts) are formed in the mixture during the course of mixing.

Patent literature 1: JP-A-2001-523217

Nonpatent literature 1: "Tooth Wear and Dentin Hyperesthesia" translated by Kenichi Kobayashi, et al., p. 357, Ishiyaku Publishers, Inc., 2003

The present invention provides an oral cavity composition containing a first composition (A) and a second composition (B) given below, said first composition (A) and said second composition (B) being discretely packed from each other so that said two compositions can be alternately used and then come to be mixed with each other at each tooth region when applied thereto:

(A) a first composition containing a fluoride ion supplying compound and an inorganic phosphoric acid or a salt thereof; and (B) a second composition containing a calcium salt of organic acid, wherein an organic acid constituting said calcium salt of organic acid has a pKa value ranging from 3 to 11, or at least one pKa value ranging from 3 to 11 when said organic acid has plural pKa values.

MODE FOR CARRYING OUT THE INVENTION

The present invention, which has been accomplished with a view to overcoming the aforementioned drawbacks of the prior art, provides an oral cavity composition with which only some ten seconds of treatment using the same yields a high effect for dental cavity prevention and an excellent dental hyperesthesia preventive and treatment effects, and a method of treatment using such a composition.

The application of the oral cavity composition according to the present invention permits an efficient uptake of a quantity of a fluoride into teeth with a brief treatment, while providing a high preventive effect against dentin hyperesthesia by calcium fluoride and calcium phosphate particles that are produced in the course of treatment and act to obturate the dental canaliculi. Further, of the oral cavity composition according to the present invention, the second composition (B), when applied to a tooth after application of the composition (A), exerts a buffer action to increase the pH value of the first composition (A) so as to reduce the acidic taste caused by the first composition (A), thus leading to an improved feeling of use as an oral cavity composition.

Besides, the present invention has permitted an efficient uptake of a fluoride in a shorter time period by using the first composition (A) and the second composition (B) as aqueous solutions thereof, with the former aqueous solution having a pH value ranging from 2 to 6 and/or the latter aqueous solution having a pH value ranging from 6 to 12. Furthermore, it may be possible to form calcium phosphate from phosphate ions contained in the first composition (A) or the tooth and calcium derived from the second composition (B) and then fix the resultant calcium phosphate onto the tooth surface. At the same time, calcium fluoride may be fixed on the tooth surface.

With the pH value of the first composition (A) below 6, a double decomposition reaction forming calcium fluoride from hydroxyapatite and a fluoride is facilitated and as a result the fluorine uptake into the tooth increases to cause the fluoride to be taken into the tooth as calcium fluoride. While, if the pH value is below 2, the calcium fluoride gets dissolved, resulting in a reduced fluorine uptake. Therefore, it is preferred that the first composition (A) according to the present invention has a pH value in the range of 2 to 6 in its aqueous solution. More preferably, the pH value ranges from 2.5 to 5.5 and further preferably from 3 to 4.5.

On the contrary, since the second composition (B) is used for neutralizing the first composition (A) to facilitate the aggregation and fixation of the calcium fluoride or calcium phosphate, it is preferred that the second composition (B) has a pH value ranging from the neutral to the alkali zone in an aqueous solution thereof Specifically, the pH value of the second composition (B) ranges from 6 to 12, more preferably from 7 to 12 and further preferably from 8 to 11.5. It is to be noted here that the pH value herein represents a value in a concentration at which the specific composition is applied to teeth, and if for example the composition is a powder and used as dissolved in water, the pH value represents that of an aqueous solution of the composition.

The first composition (A) according to the present invention is applied onto a tooth to permit the supply of fluorine ions and phosphoric acid in order to form calcium fluoride and calcium phosphate on the tooth surface.

The second composition (B) according to the present invention is used to externally supply calcium for permitting the quick formation of calcium fluoride and consequently enabling the teeth treatment to be accomplished in a shorter time period (some ten seconds), thus substantially relieving the burden on persons (especially children) under dental treatment. Besides, the concurrent formation of calcium fluoride with calcium phosphate improves the acid resistance of teeth and facilitates the remineralization of teeth, and also highly improves the effect to obturate the dental canaliculi. Further, since the second composition (B) according to the present invention has a buffering action, it is possible to increase the pH value of the first composition (A) to reduce the acidic taste caused by the first composition (A) and thus improve the feeling of use of the oral cavity composition.

Further, according to the present invention, the first composition (A) and the second composition (B) are alternately applied directly onto a tooth so that the tooth surface serves as a site where the first composition (A) and the second composition (B) are reacted with each other, which allows the aggregation of calcium fluoride or calcium phosphate to occur limitedly on the tooth surface, and consequently the present invention improves the effect for improving the uptake of calcium fluoride and calcium phosphate into teeth and thus provides a high effectiveness in dental cavity prevention and also excellent preventive and treatment effects against dental hyperesthesia.

Moreover, APF itself has not been recognized yet to have any preventive effect against dental cavities. The alternate application to the tooth of the first composition (A) and the second composition (B) according to the present invention allows the first composition (A) to cooperate with the second composition (B) containing a calcium salt of organic acid to efficiently form calcium fluoride or calcium phosphate on the tooth surface, and thus not only a high preventive effect against dental cavity but also an excellent preventive effect against dental hyperesthesia is realized according to the present invention.

Now, the efficient formation of calcium fluoride and calcium phosphate on the tooth surface realized by the cooperation of the first composition (A) and the second composition (B) according to the present invention will be described more specifically. After supplying a sufficient quantity of the first composition (A) to a target tooth region under treatment, the second composition (B) is supplied by application to the target tooth region in an excess quantity sufficient for the entirety of the first composition (A) to complete its reaction with the second composition (B). Then, the first composition (A) is supplied again to the target teeth region in an excess quantity sufficient for the entirety of the residual second composition (B) to complete the first composition (A). By repeating such a cycle, the present invention permits the first composition (A) and the second composition (B) to cooperate with each other to efficiently form calcium fluoride or calcium phosphate on the tooth surface.

According to the present invention, the fluoride ion-supplying compound is not specifically limited and may be any substance that can directly supply fluoride ions as a salt usable in a oral cavity (in other words, monofluorophosphates, which don't supply fluoride ion directly, do not fall under the fluoride ion supplying compound according to the present invention), including, for example, inorganic fluorides such as sodium fluoride, potassium fluoride, ammonium fluoride, lithium fluoride, and etc., and organic fluorides such as amine fluorides, etc., and preferred inorganic fluorides include sodium fluoride, tin fluoride, lithium fluoride and ammonium fluoride in respect of safety, solubility, flavor, or etc.

It is to be noted here that monofluorophosphates (e.g., sodium monofluorophosphate, potassium monofluorophosphate, ammonium monofluorophosphate, or etc.) may be used in combination with the above-described fluoride ion-supplying compound and calcium salt of organic acid.

If the calcium fluoride and calcium phosphate produced from the composition (A) and the composition (B) according to the present invention contain a monofluorophosphate such as sodium monofluorophosphate, the acid resistance of the teeth will be further improved. The first composition (A) and/the second composition (B) according to the present invention may contain sodium monofluorophosphate in a quantity ranging from 0.01 to 20 wt %, preferably from 0.05 to 5 wt % and more preferably from 0.05 to 2 wt %.

It is preferred that the first composition (A) of the present invention has a fluorine ion concentration in the range of 0.0025 mol/l to 1 mol/l. More preferably, the fluorine ion concentration ranges from 0.025 mol/l to 0.5 mol/l and particularly preferably from 0.05 mol/l to 0.5 mol/l.

According to the present invention, the inorganic phosphoric acids or salts thereof include, for example, alkali metal salts and ammonium salts of orthophosphoric acids such as potassium orthophosphate, sodium orthophosphate, or ammonium orthophosphate, and etc., monopotassium phosphate, dipotassium phosphate, tripotassium phosphate, monosodium phosphate, disodium phosphate and trisodium phosphate, and pyrophosphoric acids and salts thereof (e.g., sodium pyrophosphates, potassium pyrophosphates, ammonium pyrophosphates, or etc.). The inorganic phosphoric acid concentration of the first composition (A) of the present invention ranges preferably from 0.005 mol/l to 3 mol/l, more preferably from 0.05 mol/l to 1 mol/l and particularly preferably from 0.1 mol/l to 0.5 mol/l.

According to the present invention, the organic acid constituting the above-described calcium salt of organic acid has a pKa value ranging from 3 to 11 (as an aqueous solution at 25° C., ion concentration of 0 mol·dm$^{-3}$) when a single pKa value is involved, or at least one pKa value ranging from 3 to 11 when said organic acid has a plurality of pKa values. Preferably, the calcium salts are derived from organic acids having pKa value in the range of 6 to 10. Specifically, such calcium salts of an organic acid include calcium salts of polyol phosphates such as glycerophosphate, glyceryl aldehyde-3-phosphate, erythrose-4-phosphate, ribose-5-phosphate, glucose-1-phosphate, glucose-6-phosphate, inositol monophosphate, inositol hexaphosphate, fructose-1-phosphate, fructose-6-phosphate, fructose-1,6-diphosphate, ascorbate-2-phosphate, phosphorylated maltotriose, phosphorylated maltotetraose, and etc.

The calcium salt of organic acids according to the present invention include water-soluble compounds composed of organic acids and calcium such as calcium lactate, calcium acetate, calcium gluconate, calcium benzoate, calcium glycerophosphate, calcium formate, calcium fumarate, calcium butyrate, calcium isobutyrate, calcium malate, calcium maleate, calcium propionate, and etc.

It is preferred that the first composition (A) according to the present invention be used in the form of a liquid, paste or gel. It is also preferred that the molar ratio of the fluoride ion-supplying compound vs. the inorganic phosphoric acid or salt thereof (fluoride ion-supplying compound/inorganic phosphoric acid or salt thereof) of the first composition (A) according to the present invention falls in the range of 0.1 to 10.

According to the present invention, the second composition (B) is not limited to any particular state but may take any state that can supply calcium ions and permit it to mix quickly with the first composition (A) and, preferably, it is provided in the form of a liquid, paste, gel or powder. The content of the calcium salt of organic acid of the second composition (B) ranges preferably from 0.005 mol/l to 1 mol/l, more preferably from 0.01 mol/l to 0.5 mol/l and particularly preferably from 0.02 mol/l to 0.2 mol/l.

The second composition (B) according to the present invention may be used in the state of a powder or it may be supported in a state substantially free of water content on a suitable carrier. For example, the second composition (B) according to the present invention may be supported (by adhesion or mixing) on a carrier and water may be added to the carrier in use, resulting in that a high calcium concentration and buffer action can be maintained at the site of treatment action (e.g., tooth surface subjected to treatment) and the ease of use can be further improved.

In cases where the first composition (A) or the second composition (B) is a powder, the powder content may range preferably from 0.1 to 100 times, more preferably from 0.2 to 50 times and particularly preferably from 0.2 to 20 times the mass of the carrier used.

The first composition (A) and the second composition (B) according to the present invention both may be in the form of liniment, mouth wash or dentifrice, or either one may be in the form of mouth wash and the other dentifrice, or vice versa.

According to the present invention, the molar ratio of the fluoride ion-supplying compound of the first composition (A) vs. the calcium salt of organic acid of the second composition (B) is not specifically limited, but the molar ratio may range preferably from 0.02 to 50, more preferably from 0.05 to 20 and particularly from 0.2 to 5.

The carrier for the first composition (A) and/or the second composition (B) according to the present invention is not specifically limited, but may be any appropriate water absorbent material having a sufficient strength for application to the tooth surface. More specifically, appropriate materials for the carrier include paper, cloth (e.g., gauze, or etc.), non-woven fabrics (e.g., of ultrafine fibers, natural fibers, or etc.), absorbent cotton, sponges, porous films, and etc.

The above-described porous films may include celluloses, acetates, polyurethanes, porous synthetic rubbers, collagens, and etc.

Specifically, to treat a tooth by alternately applying thereto the first composition (A) and the second composition (B) according to the present invention in cases where the compositions are provided as a liquid liniment, the first composition (A) may be applied to the target site and left to stand for 5 to 10 seconds thereafter and then the second composition (B) may be applied to the target site and left to stand for 5 to 10 seconds thereafter, as well. Such a cycle may be repeated one or more times. Alternatively, the above-described process may be accomplished in reverse order, that is, the second composition (B) may first be applied to the target site and left to stand for 5 to 10 seconds thereafter and then the first composition (A) is applied to the target site to be left to stand for 5 to 10 seconds thereafter.

Also, where the first composition (A) is a mouth wash and the second composition (B) is a dentifrice, the mouth may be rinsed for 30 seconds with the mouth wash of the first composition (A) and then the teeth may be brushed for 3 minutes with the dentifrice of the second composition (B), and such a cycle may be repeated one or more times. Further, the teeth may first be brushed with the dentifrice of the second composition (B) for 3 minutes, followed by 30 seconds of mouth rinsing with the mouth wash of the first composition (A).

In cases where the first composition (A) and the second composition (B) are both provided as mouth washes, the mouth may first be rinsed for 30 seconds with the mouth wash of the first composition (A) and then rinsed for another 30 seconds with the mouth wash of the second composition (B), and such a cycle may be repeated one or more times. In use, the second composition (B) may be applied first, and then the first composition (A). When the first composition (A) is provided in the form of liniment and the second composition (B) in the form of powder, the liniment of the first composition (A) may first be applied to the target site and left to stand for 5 to 10 seconds and then the powder of the second composition (B) may be applied to the target site to be left to stand for 5 to 10 seconds thereafter. Such a cycle may be repeated one or more times. In use, the second composition (B) may be applied first, and then the first composition (A), as well.

The dosage of the fluoride ion supplying compound per one treatment (performed in one or more cycles) may range preferably from 0.1 mg to 100 mg, more preferably from 1 mg to 50 mg and further preferably from 2 to 30 mg based on the atomic weight of fluorine. Also, the dosage of the inorganic phosphoric acids or salts thereof per one treatment (performed in one or more cycles) may range preferably from 0.2 mg to 1,000 mg, more preferably from 1 mg to 500 mg and further preferably from 2 to 200 mg based on the atomic weight of phosphorus. Further, the dosage of the calcium salt of organic acid per one treatment (performed in one or more cycles) may range preferably from 0.2 mg to 1,000 mg, more preferably from 1 mg to 500 mg and further preferably from 2 to 200 mg based on the atomic weight of calcium.

In addition to the aforementioned ingredients, the oral cavity composition of the present invention may contain, for example, a foaming agent, foaming aid, abrasive, wetting agent, binder, extender, sweetener, preservative, bactericide, medicinal ingredient, self-adhesive, pigment, colorant, flavor, or etc., as appropriate. Besides, there is no limitation to the use of polyethylene glycol or like skin-lightening ingredients in combination with the oral cavity composition according to the present invention.

Furthermore, the oral cavity composition of the present invention may be prepared in the dosage form of a solution, gel, paste, or etc., for example, and may be used as a dentifrice, liquid dentifrice, mouth wash, or etc.

EXAMPLES

In the description of the preferred examples below, the percentages are all given as % by weight.

Example 1

Dental Treating Agent 1

| A | Sodium fluoride | 2% |
|---|---|---|
|   | Phosphoric acid | 1.6% |
|   | Purified water | balance |
|   | pH | 3.6 |
| B | Calcium glycerophosphate | 3% |
|   | Sodium monofluorophosphate | 1% |
|   | Purified water | balance |
|   | pH | 8.1 |

Usage: Composition A is applied first and then the composition B.

Example 2

Dental Treating Agent 2

| A | Sodium fluoride | 2% |
|---|---|---|
|   | Phosphoric acid | 3% |
|   | Purified water | balance |
|   | pH | adjusted to pH 4.0 with sodium hydroxide |
| B | Calcium glycerophosphate | 50% |
|   | Xylitol | 20% |
|   | Glycerin | 10% |
|   | Sodium monofluorophosphate | 1% |
|   | Dextrin | balance |

The ingredients are mixed together so that the total weight amounts to 50% of the swab weight.

Example 3

Dental Treating Agent 3 (Application and Mouth Rinsing)

| A | Sodium fluoride | 2% |
|---|---|---|
|   | Phosphoric acid | 2% |
|   | Sodium monofluorophosphate | 1% |
|   | Purified water | balance |
|   | Adjusted to pH 3.5 with sodium hydroxide | |
| B | Calcium lactate | 1% |
|   | Xylitol | 10% |
|   | Polyoxyethylene hydrogenated castor oil | 1% |
|   | Flavor | 0.1% |
|   | Purified water | balance |

After applying the composition A, the composition B is used to rinse the mouth.

After applying the composition A, the composition B is wetted with water and applied.

Example 4

Dentifrice and Mouth Wash

| A | Sodium fluoride | 0.21% |
|---|---|---|
|   | Phosphoric acid | 0.5% |
|   | Xylitol | 10% |
|   | Sorbitol solution (70%) | 40% |
|   | Polyethylene glycol 600 | 5% |
|   | Saccharin | 0.1% |
|   | Sodium lauryl sulfate | 1% |
|   | Silicic acid anhydride | 15% |
|   | Carboxymethylcellulose sodium salt | 1% |
|   | Flavor | 1% |
|   | Purified water | balance |
|   | Adjusted to pH 5 with sodium hydroxide. | |
| B | Calcium glycerophosphate | 1% |
|   | Sodium monofluorophosphate | 0.14% |
|   | Xylitol | 10% |
|   | Polyoxyethylene hydrogenated castor oil | 1% |
|   | Flavor | 0.1% |
|   | Purified water | balance |

After brushing teeth with the dentifrice of the composition A, the mouth is rinsed with the mouth wash of the composition B.

Example 5

Two Mouth Washes

| A | Sodium fluoride | 0.05% |
|---|---|---|
|   | Phosphoric acid | 0.2% |
|   | Sorbitol solution (70%) | 10% |
|   | Sodium lauryl sulfate | 0.2% |
|   | Flavor | 0.1% |
|   | Purified water | balance |
|   | Adjusted to pH 4.5 with sodium hydroxide. | |
| B | Calcium glycerophosphate | 1% |
|   | Sodium monofluorophosphate | 0.14% |
|   | Xylitol | 10% |
|   | Polyoxyethylene hydrogenated castor oil | 1% |
|   | Flavor | 0.1% |
|   | Purified water | balance |
|   | pH | 9.0 |

Usage: The mouth is rinsed with the mouth wash of the composition A, followed by rinsing with the B mouth wash.

COMPARATIVE EXAMPLES

Comparative Example 1

Dental Liniment (Acidulated Phosphate Fluoride Solution APF)

| Ingredients | |
|---|---|
| Sodium fluoride | 2% |
| Phosphoric acid | 1.5% |

Comparative Example 2

Dentin Desensitizer

| Ingredient | Sodium fluoride | 5% |
| --- | --- | --- |

Comparative Example 3

Dentin Hyperesthesia Preventive Dentifrice

| Active ingredient | Potassium nitrate | 5% |
| --- | --- | --- |

Comparative Example 4

| | Ingredient | % |
| --- | --- | --- |
| A | Sodium fluoride | 0.21% |
| | Xylitol | 10% |
| | Sorbitol solution (70%) | 40% |
| | Polyethylene glycol 600 | 5% |
| | Saccharin | 0.1% |
| | Sodium lauryl sulfate | 1% |
| | Silicic acid anhydride | 15% |
| | Carboxymethylcellulose sodium salt | 1% |
| | Flavor | 1% |
| | Purified water | balance |

<Evaluation of Fluorine Uptake>

1. Determination of Fluorine Adsorption on HAP Pellets

In the Examples 1 through 5, HAP pellets (10 mm×10 mm×2 mm) each were treated for 10 seconds with 10 ml of the first composition A, and then with 10 ml of the composition B for another 10 seconds. This process was repeated three times with the total treating time amounting to 1 minute for each HAP pellet. For the comparative example 1, the HAP pellet was immersed in its 10 ml solution for 4 minutes. The composition of the comparative example 2 was applied to the HAP pellet and retained in the applied state for 1 hour before removal. For the comparative examples 3 and 4, the pellets each were immersed in the respective dentifrices. The fluoride adsorbed on the surface of each HAP pellet was extracted with hydrochloric acid, and using an ion analyzer (Expandable ionAnalyzer EA 940 (made by ORION company)) with fluoride ion electrodes (ionplus-Fluoride (made by ORION company)) fluorine adsorbed on the HAP pellet was determined.

2. Results

The results of the evaluation are shown in Table 1. The Examples 1-3 achieved higher fluorine uptakes to teeth in a treating time as short as 1 minute. On the contrary, the comparative example 1 (representing the existing level of the art) took as long as 4 minutes to get the same level of fluorine uptake as achieved by the preferred examples 1 through 3, thus demonstrating the effectiveness of the present invention for the fluorine uptake in a shorter time period. The preferred examples 4 and 5 achieved the fluorine uptakes of 0.6 and 0.3 µg/cm$^2$, respectively, in a 1 minute treatment, although the comparative example 4 representing common dentifrices got only a small fluorine uptake of 0.1 µg/cm$^2$ in spite of its treating time as long as 3 minutes, that is, the preferred examples 4 and 5 of the present invention showed fluorine uptakes several times greater than the comparative example 4.

TABLE 1

| | Treating time | Fluorine uptake (µg/cm$^2$) |
| --- | --- | --- |
| Example 1 | 1 min. | 5.2 |
| Example 2 | 1 min. | 5.8 |
| Example 3 | 1 min. | 4.9 |
| Example 4 | 1 min. | 0.6 |
| Example 5 | 1 min. | 0.3 |
| Comparative example 1 | 4 min. | 4.2 |
| Comparative example 2 | 1 hr. | 2.2 |
| Comparative example 3 | 3 min. | Below detectable level |
| Comparative example 4 | 3 min. | 0.1 |

<Evaluation of Efficacy on Dentin Hyperesthesia>

1. Methodology

One hundred persons aged from 24 to 64 years suffering from dentin hyperesthesia were employed as subjects for evaluation. The subjects were divided into five groups of 20 subjects each and the subjects belonging to three groups thereof were treated for 10 seconds with the solutions of the preferred examples 1 through 3 in 3 cycle alternate treatment mode, respectively, while for the comparative examples the subjects of the remaining one group were treated for 4 minutes with APF commonly used for dental cavity prevention (comparative example 1) and the subjects of another remaining one group were treated by applying to them a 5% sodium fluoride preparation widely used in the past for the treatment of dentin hyperesthesia (comparative example 2). The efficacy of each example for dentin hyperesthesia was evaluated twice, namely, immediately after the application of the medicament of each example and 1 week thereafter, based on any changes in rational symptoms observed in each subject.

2. Results

The results of evaluation immediately after the alternate treatment with the first composition (A) and the second composition (B) of the present invention are shown in Table 2 along with the results obtained from the corresponding evaluation of the comparative examples. Most subjects having been suffering from dental hyperesthesia showed the disappearance of such symptoms of dental hyperesthesia after under going the respective alternate treatment for 1 minute with Examples 1 through 3 and they became free from hypersensitive toothache (Example 1: for 19 subjects among 20). To the contrary, the comparative example 1 showed a result that 15 subjects out of 20 did not undergo any improvement in their dental hyperesthesia symptoms even after 4 minutes of treatment and their hypersensitive toothache remained as before. Besides, as shown in Table 1, although the comparative example 1 exhibited a high fluorine uptake into teeth, its effectiveness for improvement of dentin hyperesthesia was very low.

Further, in the case of the comparative example 2 representing a formulation commonly used for the treatment of dentin hyperesthesia (nonpatent literature 1), dental hyperesthesia disappeared in 11 subjects out of 20 and an improvement of the hypersensitive toothache symptom was observed in 8 subjects, but no such improvement of dental hyperesthesia symptom was observed in 3 subjects. From this result, it was demonstrated that Examples 1 through 3 of the present invention are highly effective for improving dentin hyperesthesia.

Further, in the comparative example 2, the formulation was required to be retained in a state as it was applied onto the tooth surface for 1 hour after the application, consequently imposing the subject under treatment to not a little burden. On the contrary, the present invention requires only as short a time as 1 minute for treatment and has demonstrated realization of a substantial reduction of the burden imposed on subjects under treatment.

The results of the evaluation obtained one week after the alternate treatment with the first composition (A) and the second composition (B) of the present invention are shown in Table 3 along with the results obtained from the corresponding evaluation on the comparative examples. The preferred examples 1 through 3 counted 10, 12 and 12 subjects out of 20, respectively, who could experience the disappearance of dentin hyperesthesia symptom and retain their state free of the symptom thereafter, while the comparative example 2 had only 3 subjects who could likewise experience such disappearance of dentin hyperesthesia symptom and retain their state free of the symptom thereafter. Further, the preferred examples 1 through 3 counted 4, 3 and 1 subjects out of 20, respectively, who had dental hyperesthesia symptoms 1 week after the treatment, while the comparative example 2 counted as many as 7 such subjects out of 20. From the results above, it can be said that the present invention is effective for improving the persistence of the effect of treatment against dentin hyperesthesia.

In the alternate treatment with the first composition (A) and the second composition (B) in the preferred embodiments according to the present invention, fluoride ions and phosphoric acid were supplied by the first composition (A) and calcium ions were supplied by the second composition (B), and these ions served to form calcium fluoride and calcium phosphate at the same time on the tooth surface under treatment and in dental canaliculi so as to yield a higher treatment effect in a shorter treating time. Further, the calcium phosphate and calcium fluoride coexisting in dental canaliculi acted to promote dentin remineralization to obtrude the dental canaliculi and further provided the effect for reforming the teeth surface to improve its acid resistance and improving the persistence of the effect of treatment against dentin hyperesthesia. This demonstrated that the present invention is effective for improving dentin hyperesthesia and for preventing its recurrence.

On the contrary, in the comparative example 2, the agent used supplies only fluoride ions and calcium fluoride is formed using calcium ion supplied internally of the tooth, and further not only the tooth treatment takes time due to a high solubility of calcium fluoride, but also the persistence of treatment effect is inferior to the Examples.

TABLE 2

<Results immediately after treatment>

| | Subjects without symptom improvement (persons) | Subjects with symptom relief (persons) | Subjects symptom disappearance (persons) |
|---|---|---|---|
| Example 1 | 0 | 1 | 19 |
| Example 2 | 0 | 2 | 18 |
| Example 3 | 0 | 1 | 19 |
| Comparative example 1 | 15 | 5 | 0 |
| Comparative example 2 | 1 | 8 | 11 |

TABLE 3

<Results 1 week after treatment>

| | Subjects without symptom improvement (persons) | Subjects with symptom relief (persons) | Subjects symptom disappearance (persons) |
|---|---|---|---|
| Example 1 | 4 | 6 | 10 |
| Example 2 | 3 | 5 | 12 |
| Example 3 | 1 | 7 | 12 |
| Comparative example 1 | 16 | 4 | 0 |
| Comparative example 2 | 7 | 10 | 3 |

Further, as a result of a questionnaire on feeling of use to the subjects who underwent the treatment, it was revealed that the Examples hardly caused any problems, but many subjects treated with the comparative example 1 answered to have felt uncomfortable due to a strong acidic taste (see Table 4).

TABLE 4

<Feeling of use>

| | No uncomfortable feeling | Somewhat uncomfortable feeling | Uncomfortable feeling experienced |
|---|---|---|---|
| Example 1 | 17 | 3 | 0 |
| Example 2 | 16 | 4 | 0 |
| Example 3 | 17 | 3 | 0 |
| Comparative example 1 | 8 | 4 | 8 |
| Comparative example 2 | 11 | 9 | 0 |

<Evaluation of Efficacy of Dentifrices and Mouth Washes on Dentin Hyperesthesia>

Eighty persons aged from 24 to 64 years suffering from dentin hyperesthesia were employed as subjects for evaluation. The subjects were divided into four groups of 20 subjects each and, in the preferred example 4, 20 subjects belonging to one group brushed their teeth with the dentifrice for 3 minutes and then rinsed the mouth with the mouth wash, twice in one day. In the preferred example 5, another 20 subjects rinsed their mouths alternately with the mouth washes A and B each three times for 10 seconds each, twice in one day. In the comparative example 3, another 20 subjects brushed their teeth with the dentifrice for 3 minutes, twice in one day. In the comparative example 4, another 20 subjects brushed their teeth with the dentifrice for 3 minutes, twice in one day. One week after, each subject was checked for any changes in rational symptoms.

Consequently, 60% or more subjects treated with the preferred examples experienced the disappearance of pain, as compared with 20% or less for the comparative examples, as shown in Table 5.

TABLE 5

| | Subjects without symptom improvement (persons) | Subjects with symptom relief (persons) | Subjects symptom disappearance (persons) |
|---|---|---|---|
| Example 4 | 1 | 7 | 12 |
| Example 5 | 2 | 4 | 14 |

TABLE 5-continued

| | Subjects without symptom improvement (persons) | Subjects with symptom relief (persons) | Subjects symptom disappearance (persons) |
|---|---|---|---|
| Comparative example 3 | 10 | 6 | 4 |
| Comparative example 4 | 8 | 9 | 3 |

The alternate application of the first composition (A) and the second composition (B) according to the present invention permits an efficient uptake of a quantity of a fluoride into teeth with brief treatment, while providing a high preventive effect against dentin hyperesthesia by dental canaliculi calcium fluoride and calcium phosphate particles that are produced in the course of treatment and act to obturate the dental canaliculi. Further, of the oral cavity composition according to the present invention, the second composition (B), when applied to teeth after application of the composition (A), exerts a buffer action to increase the pH value of the first composition (A) so as to reduce the acidic taste caused by the first composition (A), thus leading to an improved feeling of use as an oral cavity composition.

The invention claimed is:

1. A method of treating teeth, comprising alternately applying a first composition (A) and a second composition (B) to a tooth:
   the first composition (A) containing a sodium fluoride and an inorganic phosphoric acid or a salt thereof,
   wherein:
      an aqueous solution of said first composition has a pH value ranging from 3 to 5.5,
      the molar ratio of said sodium fluoride to said inorganic phosphoric acid or salt thereof falls in the range of 0.1 to 10,
      the content of said sodium fluoride ranges from 0.025 mol/l to 0.5 mol/l, and
      the content of said inorganic phosphoric acid or a salt thereof ranges from 0.05 mol/l to 1 mol/l wherein said inorganic phosphoric acid or a salt thereof is orthophosphoric acid or a metal salt thereof; and
   the second composition (B) containing a monofluorophosphate and a calcium salt of polyol phosphate,
   wherein:
      an aqueous solution of said second composition has a pH value ranging from 7 to 11.5
      an organic acid constituting the calcium salt of organic acid has a pKa value ranging from 3 to 11, or at least one pKa value ranging from 3 to 11 when the organic acid has plural pKa values,
      the content of said calcium salt of polyol phosphate ranges from 0.02 to 0.5 mol/l,
      the content of said monofluorophosphate ranges from 0.05 to 5 wt % and
      said calcium salt of polyol phosphate is selected from the group consisting of calcium glycerophosphate and calcium glucose-1-phosphate.

2. The method according to claim 1, wherein the first composition (A) and/or the second composition (B) is supported on a carrier selected from the group consisting of paper, cloth, nonwoven fabric, absorbent cotton, sponge and porous film.

3. The method according to claim 2, wherein the carrier supporting the first composition (A) and/or the second composition (B) is impregnated with water immediately prior to application thereof to a tooth.

4. The method according to claim 1, wherein composition (A) is selected from the group consisting of a liquid liniment, a mouth wash, a gel, a paste, a dentifrice, and a solution.

5. The method according to claim 1, wherein composition (B) is selected from the group consisting of a liquid liniment, a mouth wash, a gel, a paste, a dentifrice, and a solution.

6. The method according to claim 1, wherein said alternately applying comprises applying composition (A) to a tooth to be treated and left to stand for a time ranging from 5 to 30 seconds and then applying composition (B) to the tooth to be treated and left to stand for a time ranging from 5 to 30 seconds.

7. The method according to claim 6, wherein said alternately applying is repeated one or more times.

8. The method according to claim 1, wherein said alternately applying comprises applying composition (B) to a tooth to be treated and left to stand for a time ranging from 5 to 30 seconds and then applying composition (A) to the tooth to be treated and left to stand for a time ranging from 5 to 30 seconds.

9. The method according to claim 8, wherein said alternately applying is repeated one or more times.

10. The method according to claim 1, wherein composition (A) is a mouthwash and composition (B) is a dentifrice.

11. The method according to claim 1, wherein the molar ratio of sodium fluoride in the first composition (A) to calcium salt of polyol phosphate in the second composition (B) ranges from 0.2 to 5.

12. The method according to claim 1, wherein the molar ratio of said sodium fluoride to said inorganic phosphoric acid or salt thereof in the first composition (A) falls in the range of 0.1 to 3.

13. The method according to claim 1, wherein the calcium salt of polyol phosphate in the second composition (B) is calcium glycerophosphate.

14. The method according to claim 1, wherein an aqueous solution of the first composition (A) has a pH value ranging from 3 to 4.5 and/or an aqueous solution of the second composition (B) has a pH value ranging from 8 to 11.5.

15. The method according to claim 1, wherein said inorganic phosphoric acid is an orthophosphoric acid.

16. The method according to claim 1, wherein said first composition (A) further contains a monofluorophosphate.

17. The method according to claim 1, wherein said second composition (B) is a powder.

* * * * *